United States Patent [19]

Kramer et al.

[11] Patent Number: 5,269,190
[45] Date of Patent: Dec. 14, 1993

[54] APPARATUS FOR THE PERFORMANCE OF RHEOLOGICAL MEASUREMENTS ON MATERIALS

[76] Inventors: Ole Kramer, Tornevangsvej 34F, DK-3460 Birkerod; Grethe Winther, Ved Ungdomsboligerne 24.1.th, DK-2820 Gentofte, both of Denmark

[21] Appl. No.: 720,423
[22] PCT Filed: Jan. 12, 1990
[86] PCT No.: PCT/DK90/00010
    § 371 Date: Jan. 16, 1991
    § 102(e) Date: Jan. 16, 1991
[87] PCT Pub. No.: WO90/08309
    PCT Pub. Date: Jul. 26, 1990

[30] Foreign Application Priority Data

Jan. 13, 1989 [DK] Denmark .................. 0149/89

[51] Int. Cl.$^5$ ............................. G01N 11/00
[52] U.S. Cl. ...................................... 73/822
[58] Field of Search ............ 73/818, 821, 822, 823, 73/825, 59, 58, 81

[56] References Cited

U.S. PATENT DOCUMENTS

| | | | |
|---|---|---|---|
| 2,325,027 | 7/1943 | Anway | 73/823 X |
| 4,383,450 | 5/1983 | Pringiers et al. | 73/81 X |
| 4,848,141 | 7/1989 | Oliver et al. | 73/81 |

FOREIGN PATENT DOCUMENTS

| | | |
|---|---|---|
| 2522362 | 8/1979 | Fed. Rep. of Germany . |
| 2935118 | 3/1980 | Fed. Rep. of Germany . |
| 3240666 | 5/1984 | Fed. Rep. of Germany . |
| 161944 | 7/1989 | Norway . |

Primary Examiner—Jerry W. Myracle
Attorney, Agent, or Firm—Watson, Cole, Grindle & Watson

[57] ABSTRACT

A universal measuring apparatus for the determination of rheological properties of viscous, viscoelastic and purely elastic materials measures said properties solely by axial movement of the mechanical measuring components of the apparatus ("axial rheometer"). the apparatus comprises a stiff metal frame (1, 2, 3) of which one horizontal part (3) is used as a mount for a force transducer (9) with little or practically no deflection at full scale load and on which an exchangeable piston-shaped holder (10) is mounted axially while the opposing part of the frame (1) forms a mount for a displacement transducer (4) of the micropositioner type which acts directly upon an axially moveable piston-shaped holder (6, 8), the micropositioner being able to cause an axial displacement and to continuously determine the axial position of the moveable piston-shaped holder (6, 8) with an accuracy of approximately 0.1 μm, thereby producing a deformation in a sample (11) positioned between the sample holders (8, 10).

8 Claims, 3 Drawing Sheets

APPARATUS FOR THE PERFORMANCE OF RHEOLOGICAL MEASUREMENTS ON MATERIALS

The present invention relates to an apparatus for the performance of rheological measurements on viscous, viscoelastic and purely elastic materials for the determination of the rheological properties of such materials. Such instruments are generally designated as rheometers, most of which belong to two main categories: Rotational rheometers and axial rheometers. Rotational rheometers measure the rheological properties of materials through a rotational action, which in some cases may be combined with a normal force measurement in the axial direction of the apparatus, while axial rheometers measure the properties exclusively through axial motion of the mechanical measuring components.

The rheological properties of purely elastic materials are usually given in terms of the modulus (stiffness) or, alternatively, in terms of the compliance. In case of simple liquids, the rheological properties are given in terms of the viscosity.

Polymeric materials are viscoelastic, i.e., they exhibit properties which are characteristic of liquids and solids, both. This means that time and shear rate together play important roles in the measurements and in the reporting of the rheological properties of polymeric materials.

Polymeric materials exhibit a stiffness which decreases with time at fixed deformation. This property is given in terms of the Stress Relaxation Modulus, $G(t)$, which therefore is a decreasing function. Correspondingly, it has been found that polymeric materials creep under a fixed load, i.e., the deformation increases with time. This is given in terms of the Creep Compliance, $J(t)$, which therefore is an increasing function. These properties may also be given in terms of the dynamic-mechanical properties for which the properties are given as functions of the angular frequency $\omega$. The stiffness properties are given by the Storage Modulus $G'(\omega)$ and the Loss Modulus $G''(\omega)$ while the creep properties are given by the Storage Compliance $J'(\omega)$ and the Loss Compliance $J''(\omega)$. $G''(\omega)$ and $J''(\omega)$ are measures of the viscous properties of the material.

The properties are linear at small deformations and small rates of deformation, i.e., the moduli are independent of the magnitude of the deformation and the viscosity is independent of the shear rate, thus making it possible to calculate one type of property from another type of property. This is, however, not the case for large deformations and/or high rates of deformation.

It is common to distinguish between the following main types of rheological measurements:

Stress-Strain measurements which for simple sample geometries may be used to calculate a modulus. In some cases a flow limit is observed. This may be given in terms of modulus and deformation at the onset of flow. Some rheometers may further allow determination of stress and strain at the break point for solid-like materials. Several test geometries for the performance of stress-strain measurements are being used.

Shear viscosity measurements which usually are perfomed at varying shear rates. This type of measurement is typically performed by shearing the liquid between two plates which rotate relative to each other (rotational viscometry) or by applying a pressure to force the liquid through a capillary (capillary viscometry).

Elongational viscosity measurements which usually are performed by stretching of a highly viscous cylinder which consequently decreases in diameter during stretching.

Stress relaxation measurements during which the decrease in stress is measured as a function of time at a maintained deformation. Several test geometries are being used.

Creep measurements during which the increasing deformation is measured as a function of time at a maintained load. Several test geometries are being used.

Dynamic-mechanical measurements during which the properties are measured as a function of frequency. Several test geometries are being used.

It is often important to be able to determine the properties of viscous, viscoelastic as well as purely elastic materials on very small quantities of sample, e.g., a few grams or less. With the hitherto known techniques this has only been possible using rotational rheological instruments. So-called Universal Testing Machines of the axial rheometer type require, however, fairly large, solid test pieces and determine polymer melt viscosity by the capillary method, a method which requires rather large quantities of sample. Universal testing machines of the axial rheometer type are not suitable for the determination of power low polymer melt viscosity by the so-called "squeezing flow" method with a constant moving plate velocity to be described below. The accuracy in the axial movement and in the determination of plate distance being insufficient in these machines in that it is an important feature of the "squeezing flow" method according to the present invention that as little as 30 mg of sample may be required for the determination of polymer melt viscosity.

The properties of viscous materials are therefore usually determined using rotational rheometers while the mechanically simpler Universal Testing Machines of the axial rheometer type are used extensively for measurements on solid materials where large test pieces can be used. Both rotational rheometers and axial rheometers may be used for the determination of the properties of viscoelastic materials, although rotational instruments usually are preferred for such measurements.

The design and use of rotational and axial rheometers are known for example from U.S. Pat. Nos. 3,933,032, 4,074,569 and 4,601,195 and from German Patent Publications Nos. 2,522,362, 2,935,118 and 3,240,666. Further, Norwegian published application No. 161,944 discloses an axial compression viscometer for measuring the viscosity of visco and viscoelastic materials, the upper sample holder of which viscometer being a plate coupled to a constant speed, hydraulic or pneumatic cylinder controlled by a position indicator giving the upper plate position with an accuracy 0.01 mm (10 $\mu$m), while the lower sample holder is mounted on three weighing cells controlled by a microprocessor with an accuracy of 10 grs of the weight of the sample in question. So far, the construction of rheometers has been based on a principle according to which one unit—the actuator—has produced a deformation in the sample while a different, separate unit—e.g. based on a strain-gauge or a linear variable differential transformer—measures the magnitude of the deformation or displacement. In practice this has meant that the best obtainable accuracy of the axial displacement has been about 1 $\mu$m. Another disadvantage of the hitherto known technique is that in order to be able to perform all the main types of rheological measurements, a laboratory has had to invest in both rotational and axial rheometers of which the universal rotational rheometers are more complicated in design, function and operation.

It is therefore an object of the present invention to provide a rheometer which operates according to the simple principle of axial movement and which is truly universal in the sense that it can perform all the above-mentioned main types of rheological measurements: Stress-strain, viscosity, stress relaxation, creep and dynamic-mechanical measurements, and which can perform these measurements on very small samples with different sample geometries and with an accuracy which is considerably better than $\pm 1$ µm for the axial displacement.

The object is obtained through a universal apparatus according to the present invention for measuring the properties of purely elastic, viscous and viscoelastic materials, and which exclusively functions by axial displacements of the sample holders of the instrument ("axial rheometer"), and which consists of a frame made from metal or a similar material, and where the upper part of the frame is used as a mount for a displacement transducer which pushes directly on a downward pointing, exchangeable piston-shaped holder which travels in the axial direction, while the lower part of the frame serves as a mount for a force transducer or digital balance which operates in the axial direction and on whose top side is mounted an upward facing, exchangeable piston-shaped holder, and where the holders are shaped in such a way that between them they can hold a sample whose rheological properties are to be determined, and it is a characteristic feature of the instrument, that the displacement transducer is a micropositioning device in the form of a high precision encoder mike and/or a micropositioner of the integral capacitance type which practically continuously both produces and with an accuracy of up to 1 nm determines the variable distance between the sample holders while the latter are producing a deformation in the material sample during a vertical displacement of up to 50 mm, and that the force transducer is capable of measuring forces with a relative accuracy of up to $10^{-7}$ of full scale, typically 40 N with an accuracy of about 0.1 mN in the whole range, and of determining the total deflection or compliance of the apparatus with an accuracy better than 0.2 µm, the deflection being less than 20 µm.

This determination of the apparatus deflection or compliance, i.e., the combined effects of bending, stretching and compression of the various apparatus components under load, is made with the aforementioned accuracy within the also aforementioned load of 40 N in letting an upper sample holder with a spherically shaped end push directly on the flat bottom of the lower sample holder, the micropositioner thereby registering the compliance travel of the apparatus and the force transducer registering the corresponding force.

It is obvious for a person skilled in the art that although the invention for reasons of simplicity are explained with the force transducer being mounted in the lower part of the frame and the displacement transducer in the upper part of the frame the inverted mounting of the transducers might just as well be used if appropriate.

It is a further characteristic of the apparatus that its construction also allows for accurate rheological measurements to be performed in the linear viscoelastic range with a total travel of the micropositioner of down to 0.01 mm (10 µm) from the first to the last measuring point, that it allows for the determination of physical dimensions and mechanical properties of both stiff and soft objects, including thickness and stiffness of soft objects such as soft contact lenses with an accuracy in thickness better than 1 µm, and that it allows for measurements of viscosity of liquids with an intermediate and high viscosity by squeezing the liquid between two parallel plates ("squeezing flow"). For this purpose the sample holders according to the invention are two horizontal plates, one of which by the micropositioner is forced towards the other with steady and constant velocity over an interval a where $0 < a < 50$ mm, and where the distance between the plates continuously is determined with an accuracy better than 0.2 µm.

It is still a further characteristic of the apparatus according to the invention that the micropositioner via the sample holders can be controlled to produce deformations which may vary in an increasing/decreasing manner either continuously or stepwise. The micropositioner may be a high precision micrometer screw driven by a DC motor with angular coding (e.g., of the type ORIEL ENCODER MIKE ®) and with a resolution of better than 0.1 µm, or, for measurements requiring a very small total travel, the micropositioner may further be of the integral-capacitance piezo translator type with a resolution of better than 1 nm.

It is yet a further characteristic of the apparatus that a manually controlled eccentric is used to produce a quick, predetermined deformation in connection with stress relaxation and creep measurements, that the exchangeable sample holders, between which a sample is positioned, are appropriately shaped for alternative performances of a number of different tests of the samples and for a quick exchange of samples, that a spring mechanism is used for forcing the upper holder firmly against the lower end of the micropositioner in order to reduce play during the up and down movement of the holder, and that the force transducer may be a simple weighing cell allowing for an immediate centering of the sample on the lower holder in the vertical centerline of the cell.

The apparatus is further provided with well-known technical means for interacting with computer equipment.

The novel features of the invention are thus that the apparatus can be used as a universal rheometer in the true sense of this expression with small physical dimensions similar to those of small rotational rheometers while having the relatively simple mechanical construction of an axial rheometer as described above, thus constituting a far more cost-effective rheometer than hitherto possible, that the apparatus according to the invention combines a small and very stiff frame with a surprising new application of a micropositioner of the high precision encoder mike type and/or of the integral capacitance type hitherto only known from an entirely different technical area (electro-optics)—a combination which now makes it possible to perform rheological measurements on very small samples and to use the rheometer according to the invention for the determination of polymer melt viscosity on very small samples by the squeezing flow method with constant velocity of the moving plate in which case the plate distance must be known with an accuracy of better than 1 µm at all loads, that the micropositioner is used both for producing as well as accurately determining the variable distance between the sample holders of the rheometer whereby the usual application of a separate displacement transducer, for example an LVDT (Linear Variable Differential Transformer), for the determination of the deformation in a sample is avoided, and that the apparatus can measure deformational changes in materials for the total travel of the displacement transducer (up to 50 mm) with considerably greater accuracy (up to 1 nm) than possible with Universal Testing Machines of the axial type.

BRIEF DESCRIPTION OF THE DRAWINGS

The invention is explained in more detail in the following with reference to the drawings which schematically and by way of example show an embodiment of the invention in that.

DETAILED DESCRIPTION OF THE PREFERRED EMBODIMENTS

Figure 1:
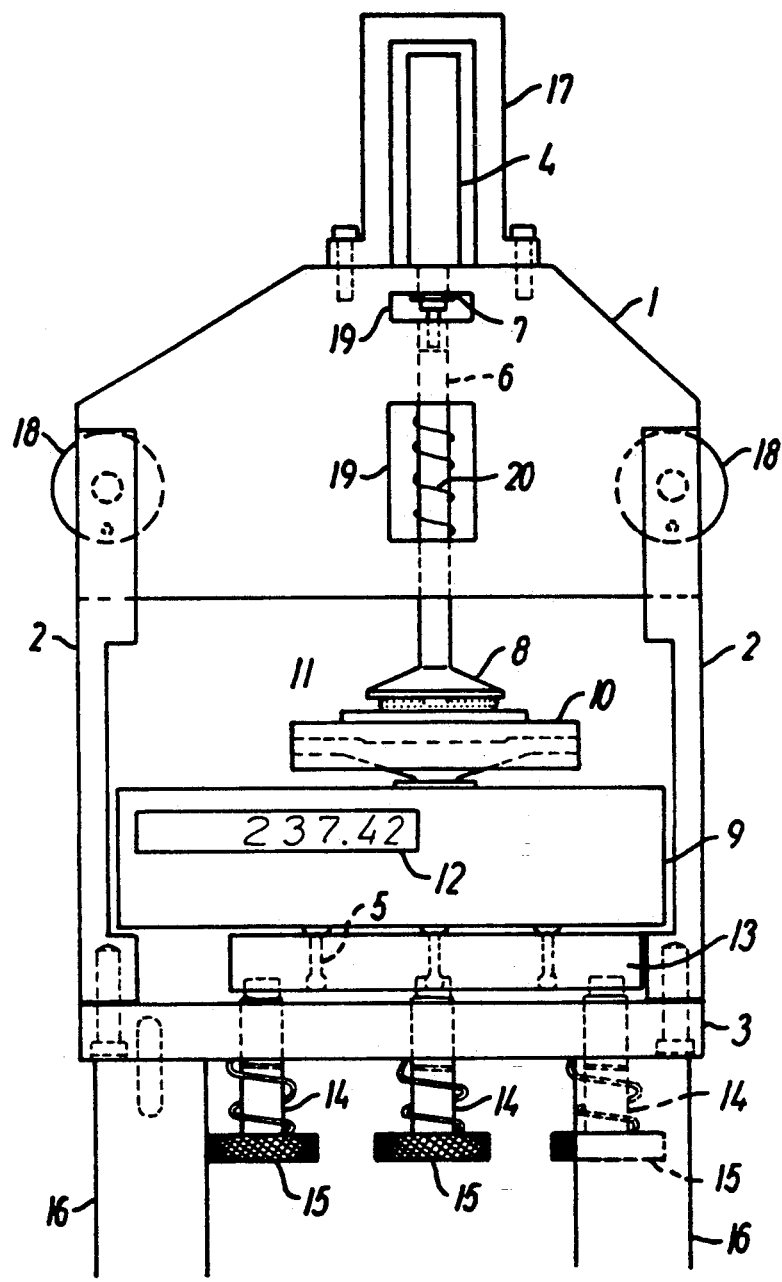
FIG. 1 is a front view of the rheometer in a version without an eccentric.

Referring now to FIG. 1, the apparatus shown comprises a solid aluminum frame with sides 2, a bottom plate 3 and a detachable upper part 1, which is fastened to the sides 2 with threaded bolts 18 with knurled, disc-shaped handles. The bottom plate 3 rests on legs 16 and is provided with three adjustment screws 14 with knurled disc-shaped handles 15 for adjustment of paralelism of the sample holders. The screws 14 carry a mounting plate 13 on which a force transducer is mounted with screws 5.

The preferred force transducer is a digital balance of the type "Mettler PM 4000" with a digital display 12. An exchangeable piston shaped holder 10 is mounted on the digital balance axially in relation to the mounting plate 13. The holder 10 may be provided with a flat surface on which a solid or a highly viscous sample 11 maybe positioned directly or on a metal plate or in a container or the like (10a in FIG. 3), and the surface may further be provided with a peripheral, vertical rim to ensure containment of liquid samples (10b in FIG. 3). Diametrically opposed vertical, upward directed knife-edged rims (10b in FIG. 3) may serve as supports for stiff, solid samples to be tested in a three-point bending procedure. A piston-shaped sample holder 8 is mounted in the upper part of the frame I axially in relation to the sample holder 10 and able to move freely in the axial direction. The upper-end 6 of the holder 8 rests against the lower-end of the micropositioner 4 which is fastened to frame 1 by means of a nut 7. The micropositioner 4 is surrounded by a protective guard 17. A coil spring 20 forces the flat end of the piston 6 against the movable end of the micropositioner 4 under a load of typically 5–10 N in order to reduce play during the up and down movements of the piston. Cut-outs 19 in the upper part of the frame 1 also allow easy servicing of the micropositioner 4 and easy exchange of upper sample holder 8.

Figure 2:
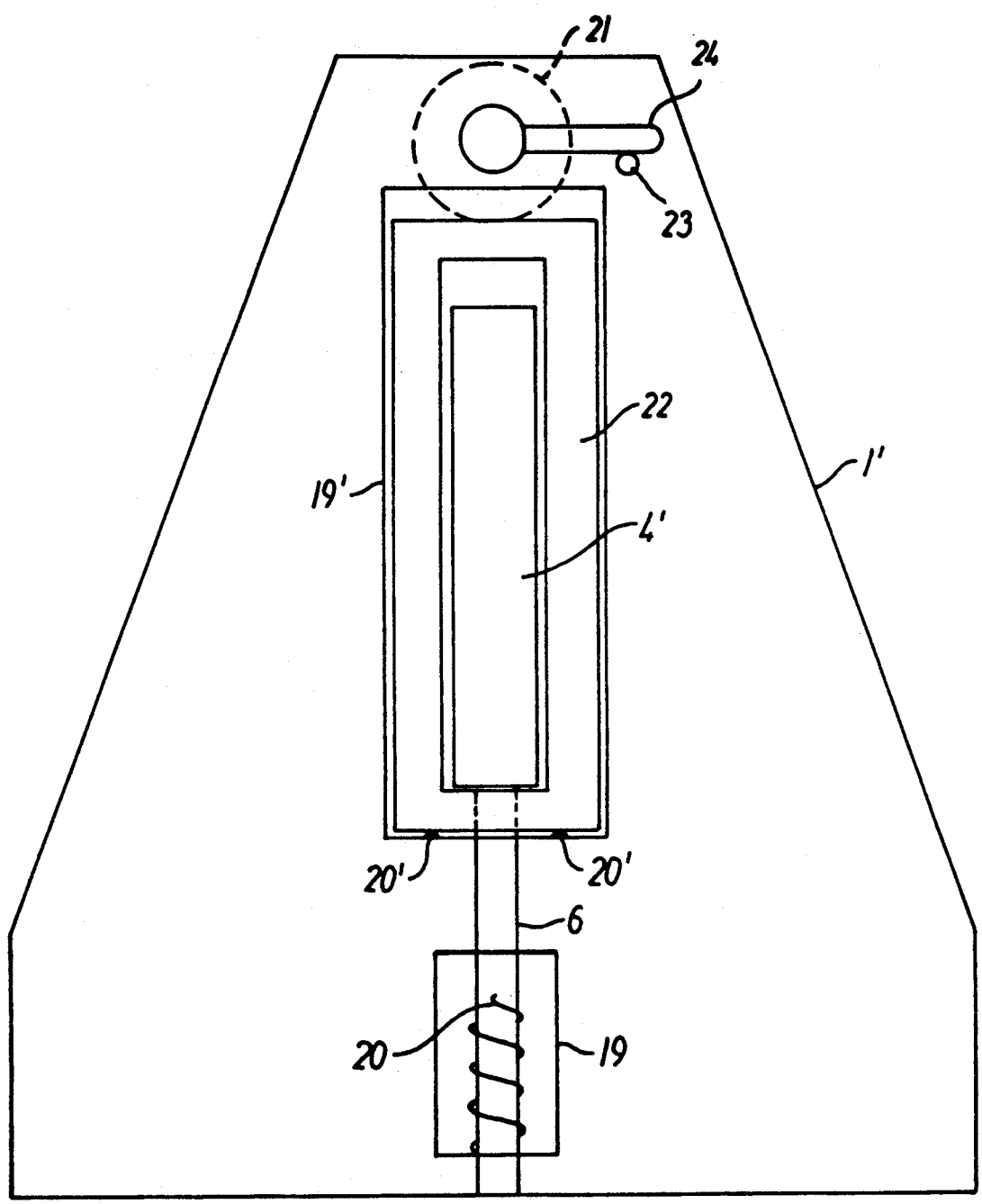
FIG. 2 shows the upper part of a frame with an eccentric for making quick step strains.

In FIG. 2 is shown the upper part of the frame 1' of another version of the apparatus. In this case an eccentric mechanism 21-24 is built into the frame to produce fast step displacements, e.g. for the performance of fast step strains in samples. A micropositioner 4' is mounted in a moveable, smaller frame 22 which slides in an opening in the frame part 1'. A circular disc 21 has been mounted eccentrically on a horizontal shaft in the upper part of the frame 1' above the smaller movable frame 22. A handle 24 is fastened to the horizontal shaft, allowing the eccentric to be turned manually. The handle 24 rests in its starting position against a stop 23 and the center of the eccentric is in this position 1 mm below the center of the horizontal shaft. Thus the eccentric in this version allows for a vertical displacement of the smaller frame 22 of up to 2 mm by a rotation of 180 degrees of the eccentric.

The smaller frame 22 and thereby the micropositioner 4' moves vertically in the upward direction under the action of coil springs 20' when the eccentric 21 is turned counter-clockwise. The magnitude of the vertical displacement may be determined by the micropositioner with an accuracy of 0.1 $\mu$m. The smaller frame 22 and thereby the micropositioner may be displaced the same distance in the downward direction in less than 0.1 s when the eccentric subsequently is turned in the clockwise direction until the handle 24 hits the-stop 23. In this manner it is possible to perform a fast and predetermined step deformation of a sample which is positioned between sample holders 8 and 10 as shown in FIG. 1.

Figure 3:
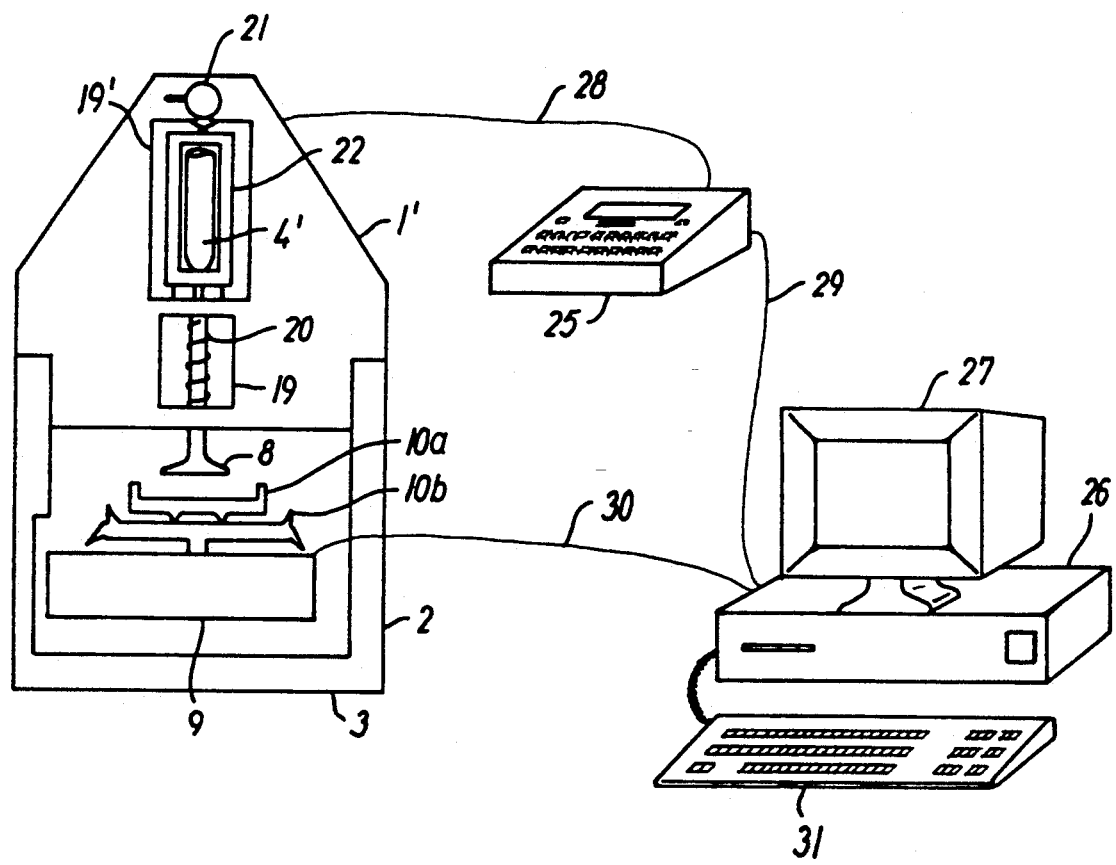
FIG. 3 shows schematically the rheometer connected to a personal computer.

In the version of the apparatus as shown in FIG. 3, the apparatus is coupled to a control and data acquisition system consisting of a microcomputer 25, which controls the micropositioner 4' via a cable 28, and a personal computer 26 which is coupled to the microcomputer 25 and to the force transducer 9 with cables 29 and 30. The computer has a monitor 27 and a key board 31. The microcomputer 25 may be programmed in a manner which allows for changes in velocity of the micropositioner 4' without intermediate complete stops. This is of importance for making dynamic-mechanical measurements on liquids.

When using the complete set-up as shown in FIG. 3, measurements are made by positioning the sample, whose rheological properties are to be determined, between the sample holders of the axial rheometer. The micrometer of the micropositioner is then started whereby the micropositioner moves the upper sample holder in the desired direction so that a deformation is produced in the sample. For simple sample geometries, the rheological properties may now be calculated on the personal computer from the force measured by the force transducer ; combined with the also measured corresponding distance between the sample holders. In a preferred embodiment of the rheometer, the micropositioner is driven by a DC motor with angular coding and the micropositioner is controlled by an "Encoder Mike Controller", the micropositioner thereby not only moving the upper sample holder but also registering the position relative to a reference position by means of the "Encoder Mike Controller". The distance between the plates is therefore continuously known, which means that the deformation in the sample may be calculated for simple geometries.

We claim:

1. Universal measuring apparatus for making rheological measurements on viscous, viscoelastic and purely elastic materials, the apparatus functioning exclusively by axial movement of its mechanical measuring components and having a frame (1, 2, 3) of metal or the like, an upper/lower horizontal part of the frame (1) being used as a mount for a displacement transducer (4) for controlling in an axial direction a downward/upward pointing, exchangeable, piston-shaped holder (6, 8) and an opposing horizontal part of the frame (3) being used as a mount for a force transducer (9) to be actuated in the axial direction and on the upper/lower side of which force transducer an upward/downward pointing exchangeable piston-shaped holder (10) is mounted, the holders further having a shape allowing to hold between them a sample (11) whose rheological properties are to be measured, and wherein the displacement transducer (4) is a high precision encoder mike with a resolution of about 0.1 $\mu$m and a total travel of up to 50 mm, the force transducer (9) measures forces with a relative accuracy of up to $10^{-7}$ and in combination with the displacement transducer allows determination of the total deflection of the apparatus with an accuracy better than 0.2 $\mu$m for the full load range of the apparatus, and the sample holders (8, 10) each have forms according to the measured material being purely elastic, viscous or visco-elastic.

2. Universal measuring apparatus according to claim 1, wherein the displacement transducer (4) is a high precision encoder mike in series with a micropositioner of the integral capacitance piezo transistor type which has a resolution of about 1 nm.

3. Universal measuring apparatus according to claim 1 for the performance of stress relaxation and creep measurements on materials, wherein it has a manually adjustable eccentric (21-24) for giving the sample a quick axial displacement the magnitude of which is determined accurately with the displacement transducer whereupon the force relaxation is measured by means of the force transducer (9) or the creep in the sample is measured by means of the micropositioner (4).

4. Universal measuring apparatus according to claim 2, wherein the eccentric mechanism (21-24) which is positioned in the upper part of the frame (1') comprises a circular disc (21) fastened eccentrically to a horizontal shaft which is provided with a handle allowing the eccentric disc to be turned relative to a reference position given by a stop (23), and in that a smaller frame (22) slidable in the vertical direction is mounted in the upper part of the frame (1') and in which smaller frame the micropositioner (4') is fastened, the smaller frame (22) being able to move up and down under the action of the eccentric disc.

5. Universal measuring apparatus with sample holders (8, 10) according to claim 1, wherein the holders are two horizontal parallel plates, or the holders are two vertical, coaxial cylinders, or the holders have vertical plates of which two outer plates individually or combined into one unit rest on the lower holder while a middle plate is mounted on the upper holder for an axial movement between the two plates of the lower holder, or the lower holder at its ends or circumference is equipped with edge-like, upwards pointing supports for carrying a horizontally place rod-like member, the bending force of which is to be measured, and the upper holder being a vertical rod or piston with a tapering lower end for yielding a mid-point pressure on the horizontal member.

6. Universal measuring apparatus according to claim 1, including a spring mechanism (20) for providing a force which acts on the upper holder (6, 8) so that the holder is in close contact with the lower end of the micropositioner (4) at all times, and so that play is counter-acted during the axial up-and-down movement of the holder.

7. Universal measuring apparatus according to claim 1, wherein the force transducer (9) consists of a single weighing cell and that the lower sample holder is mounted in such a way that the sample in question is always placed in the vertical centerline of this weighing cell.

8. A universal measuring apparatus for making rheologic measurements on viscous, viscoelastic and purely elastic material samples, said apparatus comprising:

a frame which includes a lower part and a detachable upper part and provides first and second horizontal members, a force transducer mounted on said first horizontal member for measuring a force along an axis, a first piston-shaped sample holder mounted on said force transducer, a displaceable transducer mounted on said second horizontal member and displaceable along said axis, a second piston-shaped sample holder positioned between said displaceable transducer and said first piston-shaped sample holder to provide for a material sample to be positioned and retained between said first and second holders, said displaceable transducer consisting of a high precision encoder mike with a resolution of about 0.1 $\mu$m and a total travel of up to 50 mm, and said force transducer measuring force with a relative accuracy of up to $10^{-7}$ and, together with said displacement transducer, providing a determination of the total deflection of the apparatus with an accuracy of better than 0.2 $\mu$m over a full load range of said apparatus.

* * * * *